(12) United States Patent
Hassani

(10) Patent No.: US 11,650,153 B2
(45) Date of Patent: May 16, 2023

(54) OPTICAL FIBER SENSOR

(71) Applicant: MAXWELLIAN INC., Montreal (CA)

(72) Inventor: Alireza Hassani, Montreal (CA)

(73) Assignee: Maxwellian Inc.

( * ) Notice: Subject to any disclaimer, the term of this patent is extended or adjusted under 35 U.S.C. 154(b) by 0 days.

(21) Appl. No.: 16/300,696

(22) PCT Filed: May 12, 2017

(86) PCT No.: PCT/CA2017/050577
§ 371 (c)(1),
(2) Date: Nov. 12, 2018

(87) PCT Pub. No.: WO2017/193223
PCT Pub. Date: Nov. 16, 2017

(65) Prior Publication Data
US 2020/0150037 A1    May 14, 2020

Related U.S. Application Data

(60) Provisional application No. 62/335,215, filed on May 12, 2016.

(51) Int. Cl.
*G01N 21/552* (2014.01)

(52) U.S. Cl.
CPC ..... *G01N 21/554* (2013.01); *G01N 2201/088* (2013.01)

(58) Field of Classification Search
CPC .................. G01N 21/554; G01N 2201/088
See application file for complete search history.

(56) References Cited

U.S. PATENT DOCUMENTS

| 6,466,323 | B1 | 10/2002 | Anderson et al. | |
| 7,352,468 | B2 * | 4/2008 | Tarsa | G01N 21/39 |
| | | | | 250/227.14 |
| 7,949,210 | B2 * | 5/2011 | Durfee | G02F 1/035 |
| | | | | 385/1 |
| 8,476,007 | B2 * | 7/2013 | Sai | G01N 21/7703 |
| | | | | 435/4 |

(Continued)

OTHER PUBLICATIONS

International Search Report and Written Opinion dated Sep. 15, 2017 in International application No. PCT/CA217/050577.

*Primary Examiner* — Georgia Y Epps
*Assistant Examiner* — Don J Williams
(74) *Attorney, Agent, or Firm* — Woods Oviatt Gilman LLP; Katherine H. McGuire, Esq.

(57) ABSTRACT

Plasmonic optical fibers, plasmonic optical sensors and methods of manufacturing the same. A fiber core conveys an optical signal therewithin and provides a plasmonic sensing area exposed to a fluid. The plasmonic sensing area is formed only on a section of an external surface of the fiber core. The plasmonic sensing area provides an interface within the section of the external surface for the conveyed signal to at least partially exit the fiber core and cause a modified optical signal to be conveyed in the fiber core. An optical signal generator may provide the optical signal to the plasmonic optical fiber, an optical signal receiver may discriminate the conveyed optical signal from the modified optical signal and a processor module may analyze the modified optical signal and identifies physical characteristics of the fluid present at the sensing area.

11 Claims, 10 Drawing Sheets

(56) References Cited

U.S. PATENT DOCUMENTS

| | | | |
|---|---|---|---|
| 8,675,200 B2 | 3/2014 | Suda et al. | |
| 2008/0266567 A1* | 10/2008 | Skorobogatiy | B82Y 20/00 |
| | | | 356/445 |
| 2010/0089123 A1 | 4/2010 | Fukui | |
| 2011/0267603 A1 | 11/2011 | Shaw | |
| 2013/0120752 A1* | 5/2013 | Lee | G02B 6/02 |
| | | | 356/445 |
| 2016/0334398 A1* | 11/2016 | Weissleder | B82Y 15/00 |
| 2017/0328836 A1* | 11/2017 | Lu | G02B 6/032 |

* cited by examiner

OPTICAL FIBER SENSOR

PRIORITY STATEMENT

This non-provisional patent application claims priority based upon the prior U.S. provisional patent application entitled "OPTICAL FIBER HUMIDITY SENSOR BASED ON SURFACE PLASMON", application No. 62/335,215, filed on 2016 May 12, in the name of Alireza HASSANI and Fahd BENCHEKROUN, which is hereby incorporated by reference in its entirety.

TECHNICAL FIELD

The present invention generally relates to sensors and, more specifically to humidity and gas sensors.

BACKGROUND

The monitoring of humidity help prevent corrosion, static electricity in electronic equipment environment like server rooms for example. The pharmaceutical industry, Space and Aerospace, oil & Gas industry, chemical industry, data centers, museums, archives, server rooms, healthcare, and warehouses are a few examples of environments where monitoring of humidity may be relevant. Other applications for humidity monitoring exists and can help prevent flooding or control the best range of desired humidity for better indoor air quality.

Existing humidity monitoring solution have shown limitations in accuracy, sensitivity, response time and not being Drift free.

The present invention addresses the need for humidity monitoring solution that has higher accuracy, enhanced sensitivity, faster response time and/or being Drift free.

SUMMARY

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

A first aspect of the present invention is directed to a plasmonic optical fiber comprising a fiber core for conveying an optical signal therewithin, the fiber core providing a plasmonic sensing area exposed to the fluid, the plasmonic sensing area being formed only on a section of an external surface of the fiber core. The plasmonic sensing area provides an interface within the section of the external surface for the conveyed signal to at least partially exit the fiber core and cause a modified optical signal to be conveyed in the fiber core.

The plasmonic optical fiber may further optionally comprise a fiber cladding for preventing the conveyed optical signal in the fiber core from exiting therefrom outside of the section of the external surface of the fiber core.

The interface of the plasmonic sensing area may be formed by one or more layers of material formed thereon. The one or more layer may comprise a deposited gold layer, for instance, for sensing presence of specific molecules in the fluid. The gold layer may be between 20 nm and 50 nm thick, preferably 40 nm, for sensing presence of water molecules in the fluid. A layer of glass (of about 10 nm) may optionally be added over the layer of gold. The one or more layer may also further comprise a deposited palladium layer for sensing presence of hydrogen in the fluid. In such cases, the one or more layer further comprises a deposited silver layer or tantalum layer over the gold layer for sensing presence of hydrogen in the fluid. The silver layer or tantalum layer may be 10 to 30 nm thick and the palladium layer may be 150 to 350 nm thick.

The interface of the plasmonic sensing area may be provided at an open end thereof. Alternatively, the interface of the plasmonic sensing area may be provided at one or more bends thereof.

A second aspect of the present invention is directed to a plasmonic optical sensor comprising the plasmonic optical fiber described in relation to the first aspect of the present invention, an optical signal generator for providing the optical signal to the plasmonic optical fiber, an optical signal receiver that discriminates the conveyed optical signal from the modified optical signal and a processor module that analyzes the modified optical signal and identifies physical characteristics of the fluid present at the sensing area.

A third aspect of the present invention is directed to plasmonic optical sensor comprising a first plasmonic optical fiber, an optical signal generator for providing the optical signal to the plasmonic optical fiber, a second optical fiber, an optical signal receiver and a processor module. The first plasmonic optical fiber comprises a fiber core for conveying an optical signal therewithin, the fiber core providing a plasmonic sensing area exposed to a fluid, the plasmonic sensing area being formed only on a section of an external surface of the fiber core. The plasmonic sensing area provides an interface within the section of the external surface for the conveyed signal to at least partially exit the fiber core. The second optical fiber is proximate to the plasmonic sensing area and conveys a modified optical signal from the conveyed signal to at least partially exiting the fiber core. The optical signal receiver that receives the modified optical signal from the second optical fiber. The processor module analyzes the modified optical signal and identifies one or more physical characteristics of the fluid present at the sensing area.

The plasmonic optical sensor in accordance with the third or the fourth aspect of the present invention may further comprise a fluid-permeable enclosure for housing the plasmonic optical fiber while that the sensing area is in contact with the fluid.

A fifth aspect of the present invention is directed a method of manufacturing a plasmonic optical fiber from an optical fiber. The method comprises exposing a section of an external surface of a fiber core from the optical fiber for forming a plasmonic sensing area, forming an interface within the section of the external surface such that a signal conveyed in the fiber core at least partially exits the fiber core and using microelectronic coating equipment, coating the interface with one or more layer of metal.

Forming the interface may optionally further comprise bending the exposed section of the external surface in excess of a critical angle that ensures total internal reflection of the conveyed signal therewithin. Forming the interface may alternatively further comprise cutting the fiber core for forming the interface at an open thereof.

Coating the interface with one or more layer of metal may further comprise applying a gold layer before one or more additional layer.

A sixth aspect of the present invention is directed to a method of manufacturing a plasmonic optical sensor comprising providing a fluid-permeable enclosure, positioning the plasmonic optical fiber, as defined in accordance with the first aspect of the present invention, in the enclosure for the sensing area to be in contact with the fluid and closing the enclosure for protecting the plasmonic optical fiber housed therein.

The method may further comprise positioning a second optical fiber proximate to the sensing area in the enclosure before closing the enclosure for protecting the plasmonic optical fiber and the second optical fiber housed therein.

BRIEF DESCRIPTION OF THE DRAWINGS

Further features and exemplary advantages of the present invention will become apparent from the following detailed description, taken in conjunction with the appended drawings, in which.

DETAILED DESCRIPTION

Figure 1A:
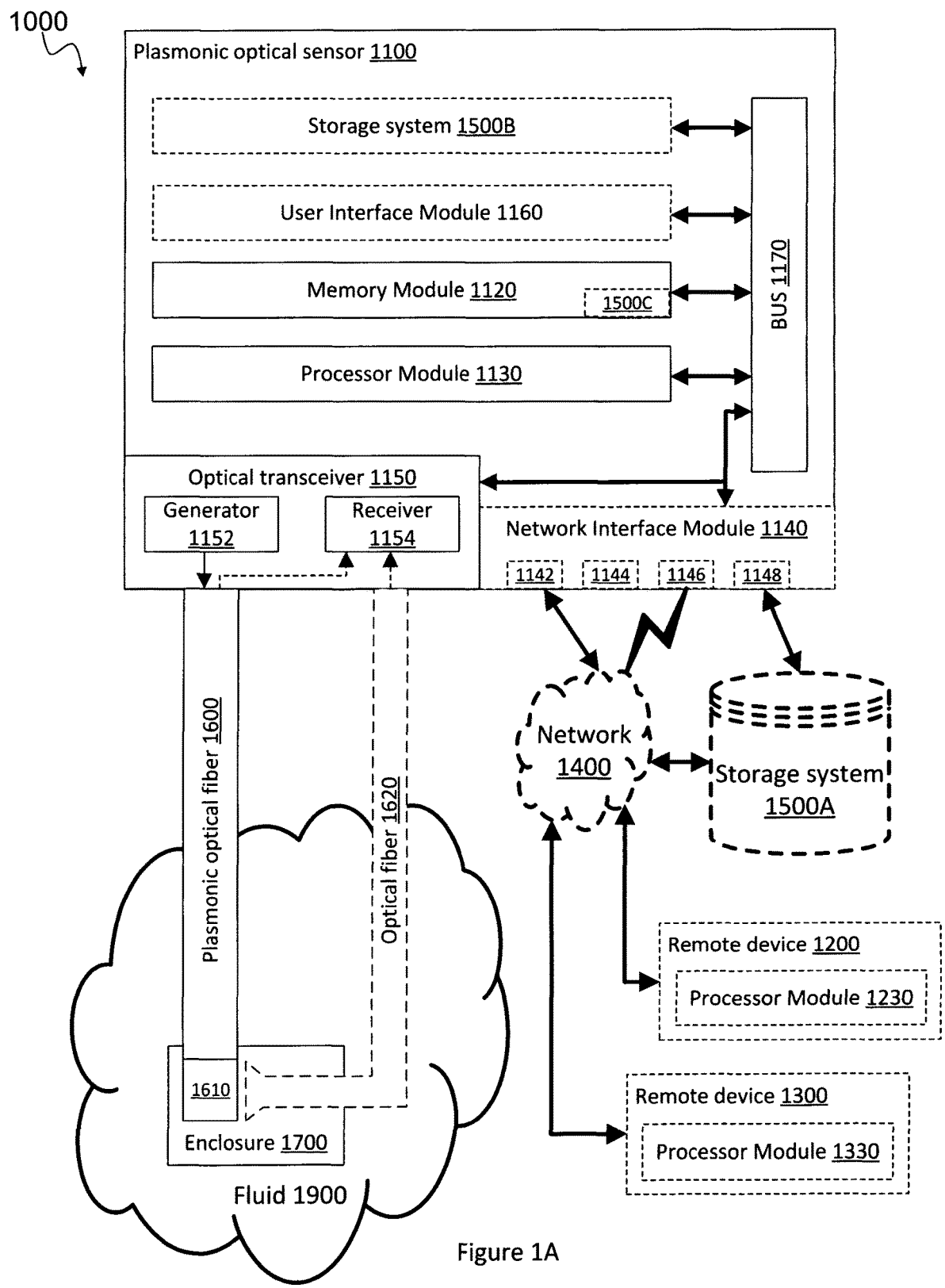
FIG. 1A and FIG. 1B, herein after referred to as FIG. 1 are logical modular representations of an environment containing a fluid in which one or more target molecules are to be detected in accordance with the teachings of the present invention.

A first category of humidity and dew sensors are electrical humidity sensors and are currently the most popular in the market. These sensors detect humidity by measuring changes in the captive characteristics of a humidity-sensitive-thin-film to measure relative humidity (RH %). Although these sensors have a relatively simple design and low price of the interrogation, the need for regular calibration, the difficulty in measuring RH % below 5% and over 90%, poor linearity and relatively long response time (up to even minutes), and not being drift free are disadvantages. Moreover, the use of electronic humidity sensors in harsh environments, explosive atmospheres or area with high electromagnetic interference is dangerous or inefficient.

Optical fiber technology may be used for sensing humidity, for instance, relying on evanescent wave interactions, Bragg grating, long-period fiber grating, and interferometers to detect humidity. Optical fiber humidity sensors typically require a hygroscopic material with optical properties sensitive to humidity change. The optical properties change in the material can be measured by absorption or phase of light reflecting back from the material, allowing the sensor to measure the humidity.

Generally, the present invention is concerned with humidity and/or gas detection, monitoring and/or measurement based on the interaction of surface plasmon waves with humidity (i.e., water) and gases. An optical detector or spectrometer is capable of detecting and/or measuring the interaction of surface plasmon waves considering phase shifting and/or absorption of an optical signal (e.g., light) controllably conveyed in the optical fiber. The interactions may be provoked by presence of molecules such as water molecules or certain gas molecules such as hydrogen. A sensing area is provided by an external surface of an optical fiber in order to expose at least a portion of the optical signal traveling in the optical fiber at the sensing area. As such, the sensing area facilitates the interaction of surface plasmons with humidity and/or gases. In some embodiments, the sensing area may be formed by a polished, taped or tapered surface at an end of the optical fiber. In some embodiments, the sensing area may be provided by a controlled bending or shaping of a continuous optical fiber. The external surface of the optical fiber forming the sensing area at the bent may also further be polished or otherwise modified to increase the interaction of light with humidity and/or gases. In some embodiments, the sensing area may be coated with one or several layers of metal, polymer and/or other material, for the purpose of increasing the interaction of light with humidity and/or gases. Different coatings may be used for different purposes (e.g., different sensitivity, different robustness and/or different target molecule). Sensitivity of the sensor to water molecules and/or gas molecules may therefore be adapted. The coating material may be uniform or non uniform with different shape or pattern, for the same purpose.

In accordance with the teachings of the present invention, plasmonic effects are relied upon to detect, monitor and/or measure humidity and/or gas. An optical signal (e.g., light from a LASER) is controllably conveyed in an optical fiber and excites plasmon waves at a sensing area formed on an external surface of the optical fiber. For instance, the sensing area may be covered by a gold layer deposited on a surface of the optical fiber interfacing with the optical signal. Plasmon waves are very sensitive to certain changes (e.g., any change in humidity, gas composition or refractive index adjacent to sensing area), resulting in predictable signal loss and/or phase shift of the optical signal in relation to certain characteristics of a gas or liquid (e.g., water or hydrogen) present at the sensing area. The optical signal conveyed in the optical fiber is therefore modified at the sensing area. The modified optical signal can then be read (e.g., measured or otherwise obtained) and analyzed for the purpose of detecting, monitoring and/or measuring humidity and/or gas at the sensing area. For instance, the modified optical signal can be measured from outside the optical fiber (e.g., by another optical fiber "reading" the output at or near the sensing area) or may, alternatively or in addition, be "read" from within the optical fiber (e.g., an optical source conveys the optical signal at one end of the optical fiber and an optical receiver discriminates the conveyed optical signal from the modified optical signal at the other end of the optical fiber). Using different embodiments of the present invention, it is possible to provide plasmonic optical fiber humidity and/or gas sensors, and methods of using the same, that meet required sensitivity, accuracy and/or response time considering acceptable cost.

In accordance with the present invention, different embodiments are provided. In a first embodiment, a plasmonic optical fiber is provided, which can be used with a correspondingly configured optical transceiver system. In a second embodiment, a plasmonic optical sensor is provided comprising an optical transceiver and processing capabilities. In a third and a fourth embodiments, methods of manufacturing, respectively, a plasmonic optical fiber and a plasmonic optical sensor are provided.

For the sake of simplicity, the first and second embodiments will be described together with reference to FIGS. 1 and 3 to 6 while the third and fourth embodiments will be described together with reference to FIG. 2 event though the different embodiments are capable of being used independently.

Figure 1B:
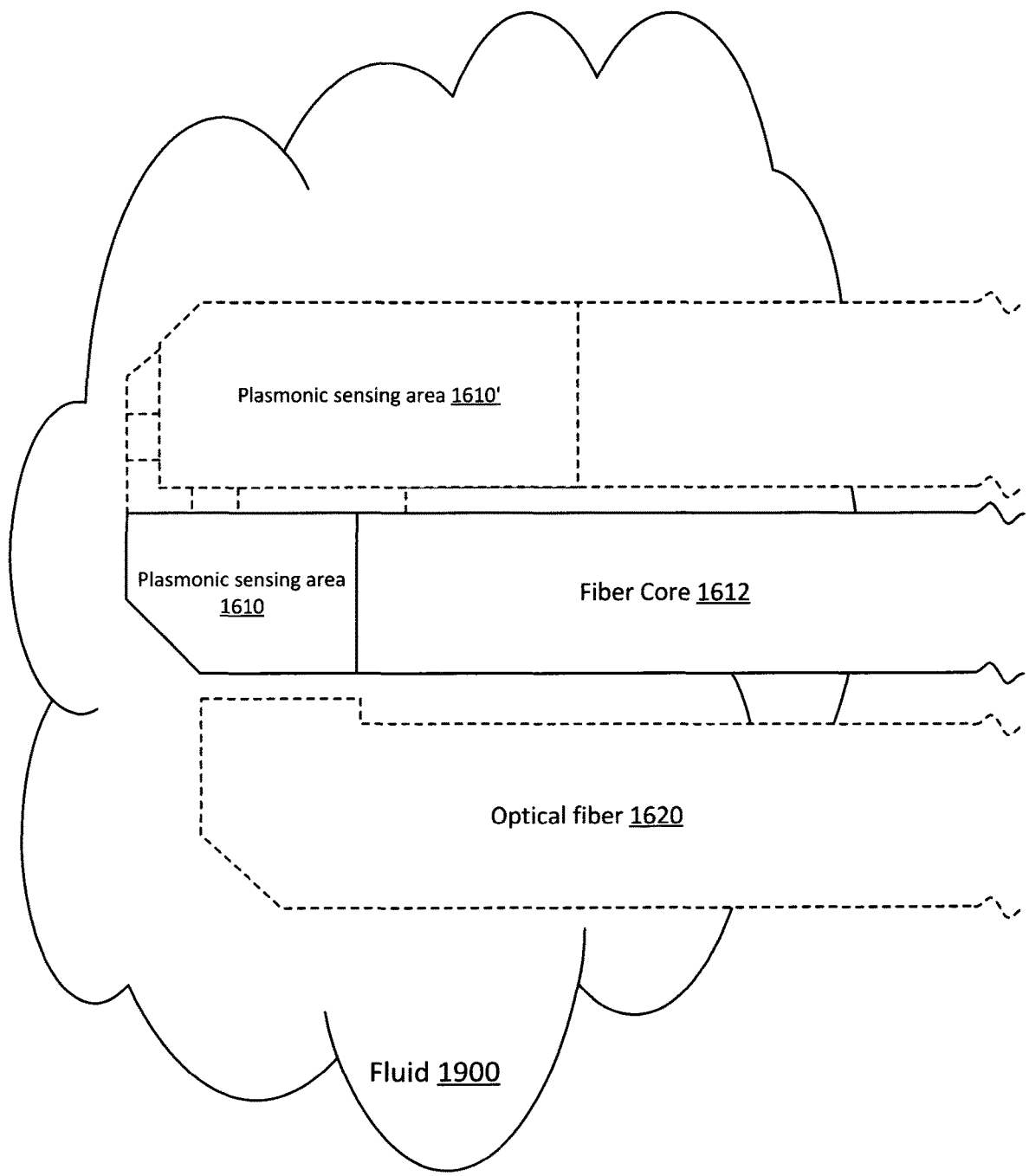

Reference is now made to the drawings, in which FIGS. 1A and 1B, together referred to as FIG. 1, show logical modular views of an environment 1000 in which an exemplary plasmonic optical sensor 1100 is deployed. The plasmonic optical sensor 1100 is for sensing humidity and/or gases present in a fluid 1900 in which a plasmonic optical fiber 1600 is deployed. The plasmonic optical fiber 1600 comprises a plasmonic sensing area 1610 that provides an interface allowing interactions of surface plasmon waves with the fluid 19000. The plasmonic optical fiber 1600 is typically housed in an enclosure 1700 that is permeable to the fluid 1900 while otherwise generally protecting the sensing area 1610. The plasmonic optical sensor 1100 may, itself, be in the fluid 1900 (e.g., the fluid 1900 is a surrounding gas) or may be distant from the fluid 1900. The plasmonic optical sensor comprises a processing module 1130, a memory module 1120 and may also comprise a storage system 1500.

In some embodiments, the plasmonic optical sensor 1100 may comprise a network interface 1140 providing a network presence therefore (e.g., remote management and/or remote operation). In the depicted embodiment of FIG. 1, remote networked devices 1200 and 1300 ae depicted that that may send one or more request to the plasmonic optical sensor 1100. The remote devices and the plasmonic optical sensor 1100 1100, 1200 and 1300 may be connected via a network 1400, via direct connections or a mix of direct and network connections. Various network links may be implicitly or explicitly used in the context of the present invention. While a link may be depicted as a wireless link, it could also be embodied as a wired link using a coaxial cable, an optical fiber, a category 5 cable, and the like. A wired or wireless access point (not shown) may be present on links. Likewise, any number of routers and/or switches (not shown) may be present on links, which may further transit through the Internet.

The processing module(s) 1130, 1230 and/or 1330 may represent a single processor with one or more processor cores or an array of processors, each comprising one or more processor cores. The memory module 1120 may comprise various types of memory (different standardized or kinds of Random Access Memory (RAM) modules, memory cards, Read-Only Memory (ROM) modules, programmable ROM, etc.). The network interface module 1140 typically represents at least one physical interface that can be used to communicate with other network nodes. The network interface module 1140 may be made visible to the other modules of the computer system 1100 through one or more logical interfaces. The actual stacks of protocols used by the physical network interface(s) and/or logical network interface(s) 1142, 1144, 1146, 1148 of the network interface module 1140 do not affect the teachings of the present invention. The variants of processing module 1130, memory module 1120 and network interface module 1140 usable in the context of the present invention will be readily apparent to persons skilled in the art.

A bus 1170 is depicted as an example of means for exchanging data between the different modules of the plasmonic optical sensor 1100. The present invention is not affected by the way the different modules exchange information between them. For instance, the memory module 1120 and the processing module 1130 could be connected by a parallel bus, but could also be connected by a serial connection or involve an intermediate module (not shown) without affecting the teachings of the present invention.

Likewise, even though explicit mentions of the memory module 1120 and/or the processing module 1130, or explicit mentions of other modules in the remote devices 1200 and 1300, are not made throughout the description of the various embodiments, persons skilled in the art will readily recognize that such modules are used in conjunction with other modules to perform routine as well as innovative steps related to the present invention. Similarly, at least one more plasmonic optical sensor (not shown) may be involved sensing humidity and/or gases present in a fluid 1900. The multiple plasmonic optical sensors may be connected (e.g., though the network 1400) and act as a single tool from the perspective of a requestor.

The plasmonic optical sensor 1100 comprises an optical transceiver 1150 comprising an optical signal generator 1152 and an optical signal receiver 1154. In the depicted example of FIG. 1, the optical transceiver is integrated with the plasmonic optical sensor 1100. Skilled persons will readily recognize that the optical transceiver may be a distinct module (not shown) connected to the processing module 1130 and/or the memory module 1120. Likewise, the generator 1152 and the receiver 1154 may also be provided in independent modules and/or as external light sources/light detectors.

FIG. 1 also shows examples of the storage system 1500 as a distinct database system 1500A, a distinct module 1500B of the computer system 1100 or a sub-module 1500C of the memory module 1120 of the plasmonic optical sensor 1100. The storage system 1500 may be distributed over different systems A, B and/or C or may be in a single system. The storage system 1500 may comprise one or more logical or physical as well as local or remote hard disk drive (HDD) (or an array thereof). The storage system 1500 may further comprise a local or remote database made accessible to the plasmonic optical sensor 1100 by a standardized or proprietary interface or via the network interface module 1140. The variants of storage system 1500 usable in the context of the present invention will be readily apparent to persons skilled in the art.

In some embodiments, the plasmonic optical sensor 1100 comprises a user interface module 1160 for allowing interactions with one or more users (not shown). The interactions with users(s) may also be made, in addition or alternatively, remotely via the network interface module 1140 on a dedicated remote user interface (not shown) or a graphical user interface (not shown) displayed on a remote device. Skilled persons will readily understand that the reference to user interface module 1160 is made for simplicity and that other types of interfaces may be used for providing similar features as the optional user interface module 1160. For instance, a smartphone, a tablet, a phablet, a computer (e.g., portable or fixed to a mobile unit) or other multi-purpose processing device may provide the user interface. The remote device 1200/1300 may be in communication with the plasmonic optical sensor 1100 (e.g., using Bluetooth or other short-range wireless protocol, over WIFI, over Ethernet, over USB, etc.).

In some embodiments, the user interface module 1160 may provide one or more buttons and/or dials (logical or physical, not shown) for adjusting settings of the plasmonic optical sensor 1100. The user interface module 1160 may also comprise an output system for displaying or otherwise conveying a meaningful measurement made by the plasmonic optical sensor 1100. For instance, the output system may simply provide a sound or alarm when a threshold for a target molecule present in the fluid 19000 is crossed. The output system may also provide, in addition or alternatively, a valued measurements for the target molecule (e.g., displayed numerically or as a moving needle over a scale). In some embodiments, alternatively or in addition, the user interface module 1160 provides a graphical user interface allowing the use thereof to adjust settings and/or obtain measurement(s) from the plasmonic optical sensor 1100.

The plasmonic optical fiber 1600 comprises a fiber core 1612 for conveying an optical signal therewithin. The fiber core 1612 provides the plasmonic sensing area 1610 exposed to the fluid 1900. The plasmonic sensing area 1610 is formed only on a section of an external surface of the fiber core. The plasmonic sensing area 1610 provides an interface within the section of the external surface for the conveyed signal to at least partially exit the fiber core 1612 for allowing a modified signal to be generated from conveyed signal. In a preferred set of embodiments, the modified optical signal is conveyed in the fiber core 1612 itself. In some embodiments, in addition or alternatively, the optional optical fiber 1620 is positioned proximate to the plasmonic sensing area 1610 in the enclosure 1700 and reads, reads, or is otherwise made to convey a signal from the light signal that at least partially exits the fiber core 1612 at the sensing area 1610. For the sake of simplicity, the signal conveyed by the second optical fiber 1620 will be referred as the modified signal (i.e., the signal that contains optical information for the purpose of detecting the target molecules). Skilled people will recognize that the modified signal conveyed by the second optical fiber 1620 is different from the modified signal conveyed by the plasmonic optical fiber 1600. The second optical fiber 1620, when provided, may be provided in a single wire (not shown) that also contains the plasmonic optical fiber 1600 and connects the enclosure 17000 to the plasmonic optical sensor 1100.

The plasmonic optical fiber 1600 typically also comprises a fiber cladding (not shown on FIG. 1) for preventing the conveyed optical signal, and potentially the modified optical signal, in the fiber core 1612 from exiting therefrom outside of the section of the external surface of the fiber core 1612.

The interface of the plasmonic sensing area 1610 is typically formed by one or more layers of material formed thereon such a deposited gold layer for sensing presence of specific molecules in the fluid. In tests performed, it has been established that a gold layer between 20 nm and 50 nm thick is proper for sensing presence of water molecules in the fluid. A thickness of 40 nm has been shown to be particularly effective. In some embodiments, a deposited palladium layer and a deposited silver or tantalum layer are deposited over the gold layer, which has been shown to be particularly effective at detecting hydrogen in the fluid.

The silver layer or tantalum layer is 10 to 30 nm thick. The palladium layer is 150 to 350 nm thick.

In some embodiments, the interface of the plasmonic sensing area 1610 is provided at an open end thereof, as will be particularly illustrated with reference to FIG. 5. In other embodiments, the interface of the plasmonic sensing area 1610 is provided at one or more bends thereof, as will be particularly illustrated with reference to FIG. 6.

In use, the optical signal generator 1152 provides an optical signal to the plasmonic optical fiber 1600, which is conveyed to the plasmonic sensing area 1610. Interactions of the conveyed signal and the fluid 1900 are possible because of the configuration of the interface at the sensing area 1610 that allows the conveyed signal to at least partly exit the fiber core 1612 thereat. The interactions cause a modified signal to be obtained in the fiber core 1612 and/or n a second optical fiber 1620. The optical signal receiver 1154 receives the modified optical signal (e.g., from the plasmonic optical fiber 1600 and/or from the second optical fiber 1620). The modified signal is then provided to the processor module 1130 that analyzes the modified optical signal and identifies one or more physical characteristics of the fluid 1900 present at the sensing area 1610.

Figure 3:
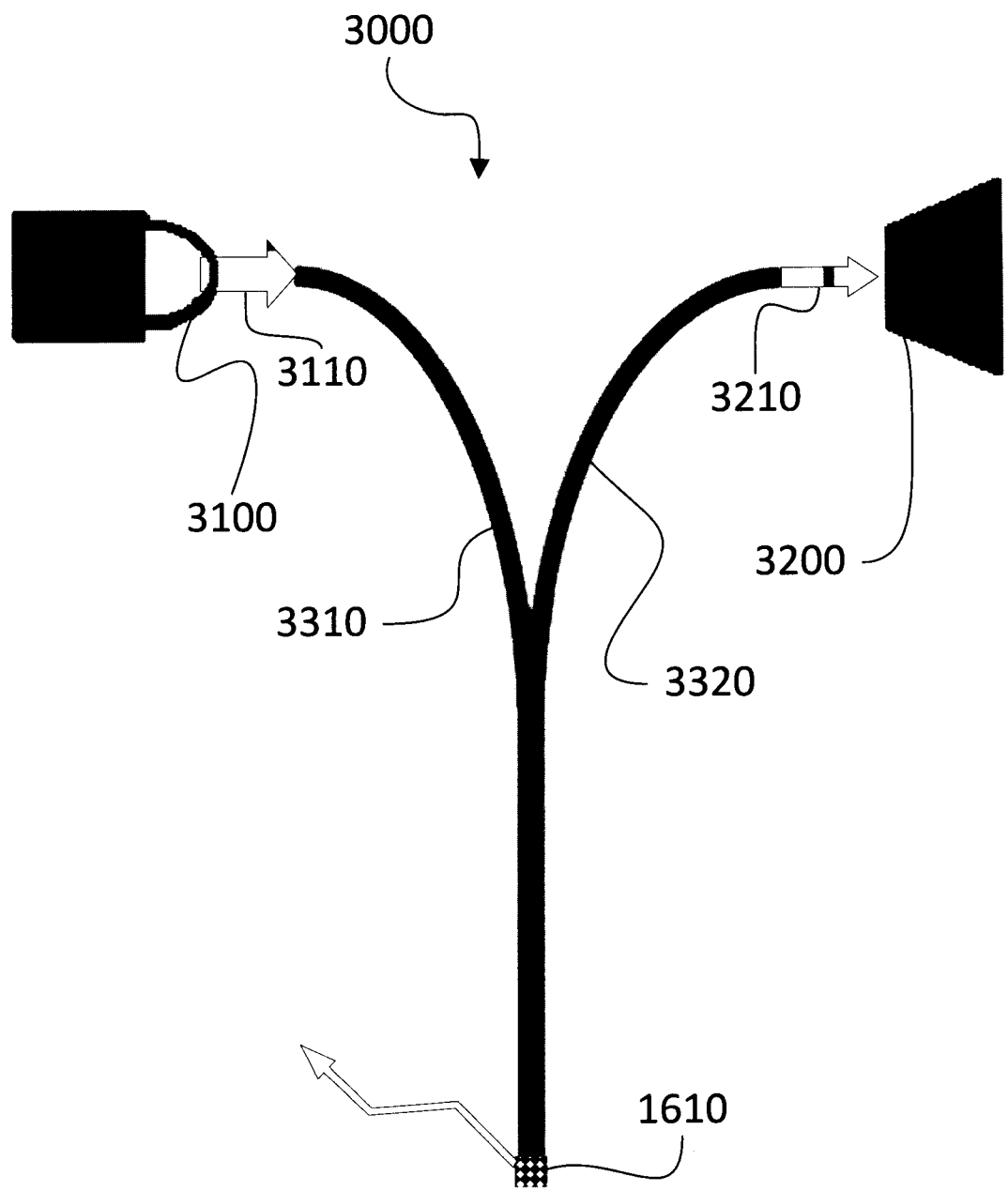
FIG. 3 is a logical representation of a first exemplary surface plasmon optical fiber humidity sensor in accordance with the teachings of the present invention.
Figure 4:
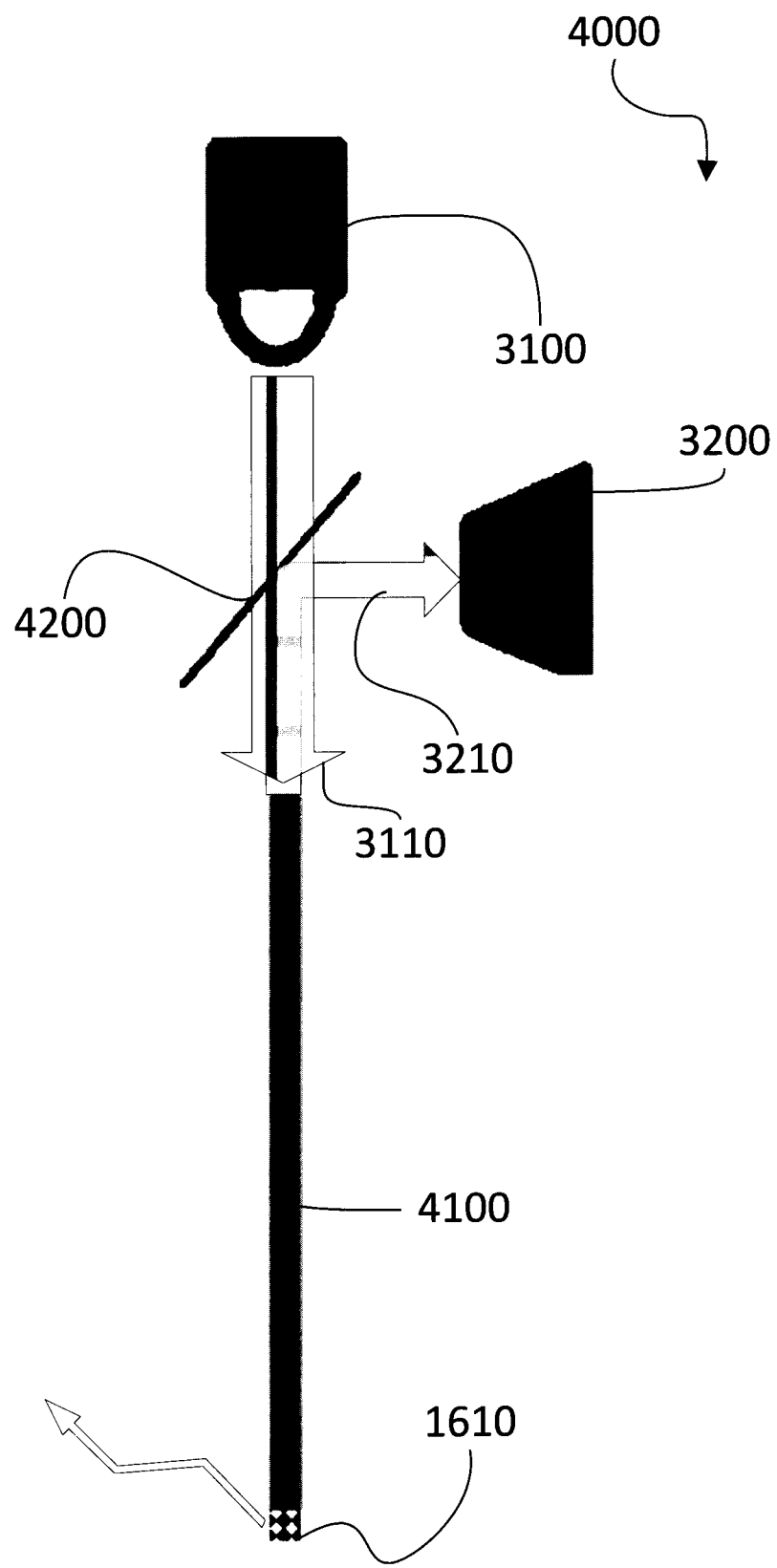
FIG. 4 is a logical representation of a second exemplary surface plasmon optical fiber humidity sensor in accordance with the teachings of the present invention.
Figure 5A:
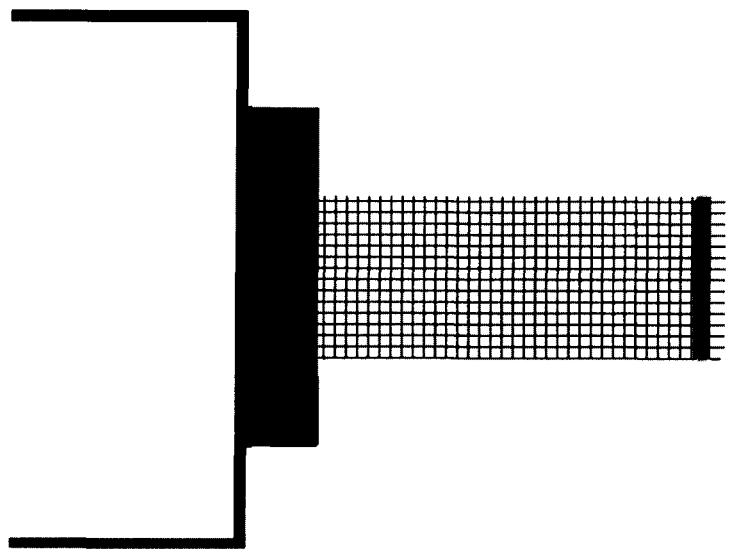
FIGS. 5A, 5B, 5C, 5D and 5E, herein referred to concurrently as FIG. 3, are logical views of different exemplary shapes for a terminal sensing area in accordance with the teachings of the present invention.
Figure 5B:
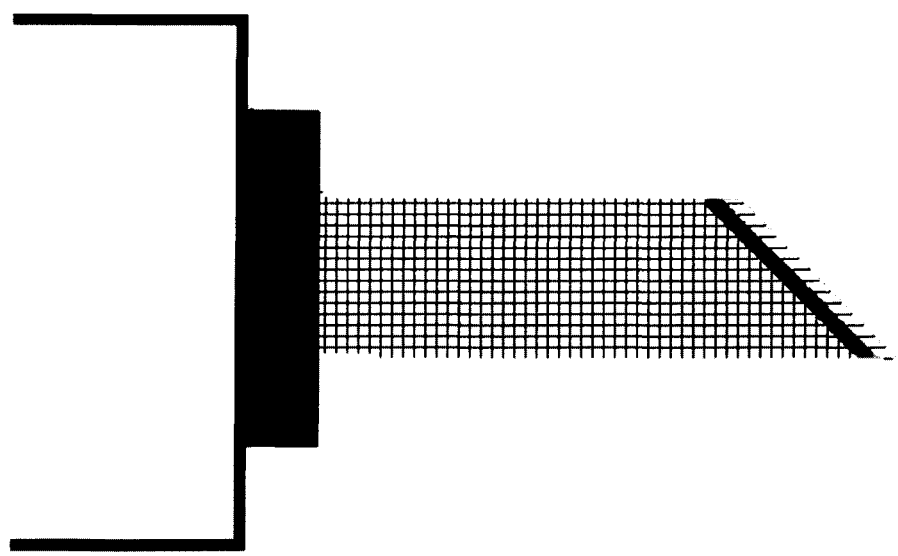
Figure 5C:
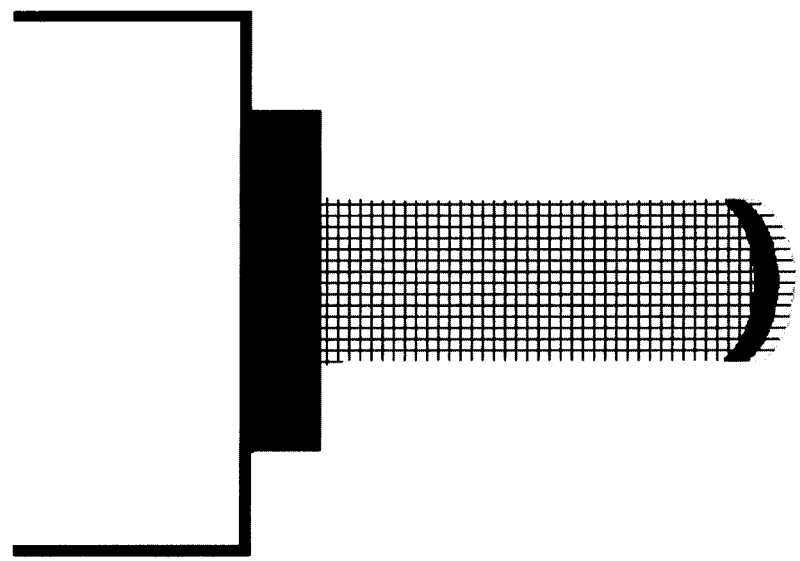
Figure 5D:
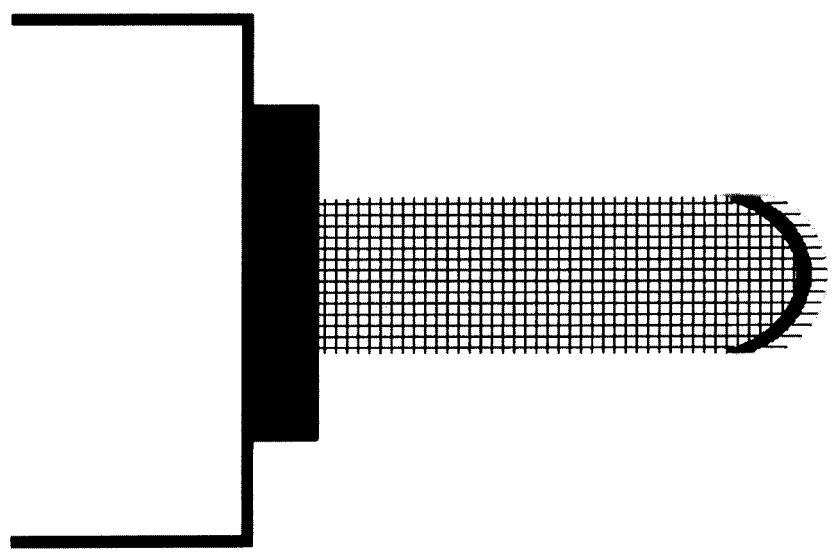
Figure 5E:
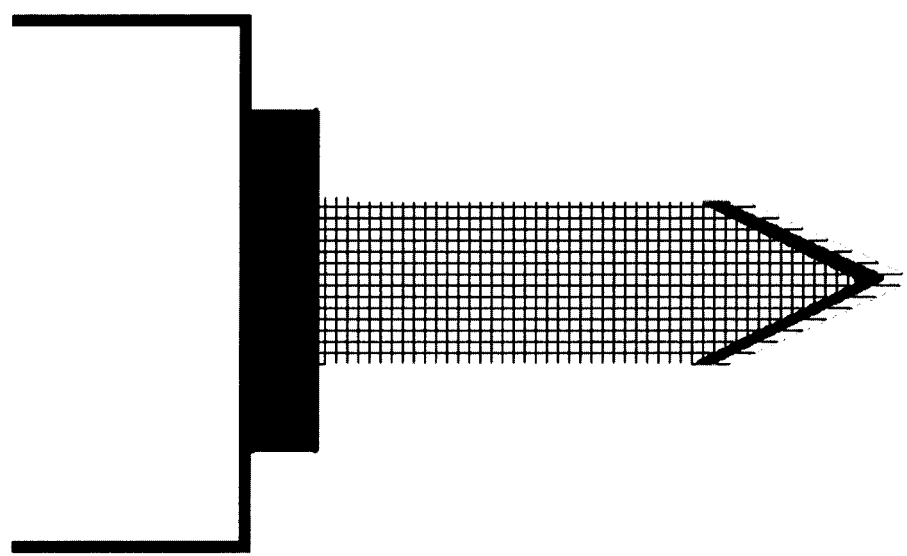

Reference is now made concurrently to FIGS. 1 and 3 to 6. FIG. 3 depicts an exemplary embodiment 3000 using a bifurcated optical fiber 3300. FIG. 4 depicts an exemplary embodiment 4000 using a single optical fiber 4100. FIGS. 5 and 6 respectively present examples of different standard and arbitrary optical fiber tip-shapes and examples of bent fiber configurations for providing the sensing area.

In FIG. 3, the bifurcated optical fiber 3310 receives an optical signal 3110 from a source 3100. When the optical signal 3110 reaches the sensing area 1610 and excites the surface plasmon waves, then the surface plasmon wave interacts with humidity and a modified signal 3210 is conveyed in a second fiber 3320 to a photodetector or any optical detector 3200. In some embodiments, the sensing area 1610 is polished and then coated with a 40 nm gold layer and may further be coated with some other glass layers to protect and enhance the sensitivity of sensors (e.g., about 10 nm in thickness). It is assumed that the glass layer, when properly applied, does not significantly interfere with the plasmonic waves tails (~1000 nm). Even if the glass layer was shown to cause some level of interference with the plasmonic waves, such interference do not prevent a meaningful and predictable detection to be made at the sensing area 1611 to the extent that it is properly applied. The optical signal 3110 entering the sensing area 1610 excites the surface plasmon resonance waves on the top of gold layer. These waves are very sensitive to any index change because of humidity or water in ambient air adjacent to the sensing area 1610 as well as any tiny consolidation or evaporation on sensing area.

Even small changes in relative humidity (RH %) between 0% to 100% can be detected by surface plasmon resonance. As the RH % changes, the optical absorption or phase due to SPR resonance peak will change, which is detectable by the optical detector 3200. For instance, the fluid 1900 may be ambient air and minute RH % change in the ambient air around the sensing area 1610 can be mapped to optical loss or phase change. Change in optical loss or phase can be calibrated to show RH % and dew point (e.g., the processing module may be an electrical signal-processing box. In one example, using the embodiment depicted on FIG. 3, a 1 nm plasmonic peak shift is detected per RH % with response time less than 0.05 second, which means that the sensor 1100 may then be made to detect 0.01RH % variations.

In FIG. 4, a fiber 4100 fiber is provided with the optical signal 3110, interacts at the sensing area 1610 with the fluid 1900 and a modified signal is generated within the fiber 4100.

In some embodiments, a multi-channel system may be used to detect humidity, dew point and/or gas(es) in multiple configurations simultaneously, using different configurations such as the ones depicted, in FIGS. 3 and 4, at once. Existing optical fiber infrastructures may also be used together with the plasmonic optical fiber 1600 and/or plasmonic optical sensor 1100. In smart buildings for example, the level of humidity may be monitored for Indoor Air Quality (IAQ) purposes. Pharmaceutical facilities may also be monitored in order to maintain humidity levels required to prevent moisture, which would otherwise increase the rate of decomposition and shorten effective life of drugs and medication. Many industries that are sensitive to the humidity level may advantageously use embodiments of the present invention. For instance, industrial manufacturing, instrumentations, space & Airspace industry, oil & gas industry, power plants, testing facilities, and museums, amongst others, may benefit from proper humidity monitoring. Embodiments of the present invention may prevent harmful effects on artwork and rare documents, manufacturing operations and normal functioning of electronic equipment, amongst many other uses.

FIG. 5 provides different examples of terminal shapes when the sensing area 1620 is provided at an end of the plasmonic optical fiber 1600. FIG. 5A shows a flat (e.g., flat polished) configuration. FIG. 5B shows an angled configuration (e.g., Angle Polished Connector (APC)). FIGS. 5C and 5D show rounded configurations (e.g., respectively Physical Contact (PC) and Ultra Physical Contact (UPC)). FIG. 5E shows an arbitrarily angled configuration. In common use of optical fibers, the purpose of selecting a terminal shape is to minimize the back reflection. In the case at hand, the concern is on the interactions with plasmonic waves as the terminal shape interfaces with the fluid 1900

FIGS. 6A, 6B, 6C, 6D depicts different examples of bent plasmonic optical fiber sensors for Humidity, Dew Point & Gas sensing. Recent tests tend to show that, although the exemplary configurations of FIG. 5 may be use to achieve interesting results, the configurations from FIG. 6 provide better results in terms of design, manufacturing and, ultimately, commercialization.

Figure 6A:
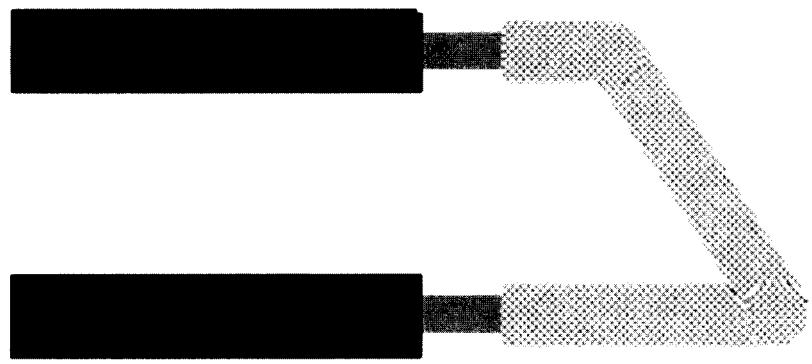
FIGS. 6A, 6B, 6C and 6D, herein referred to concurrently as FIG. 3, are logical views of different exemplary shapes for a bent sensing area in accordance with the teachings of the present invention.
Figure 6B:
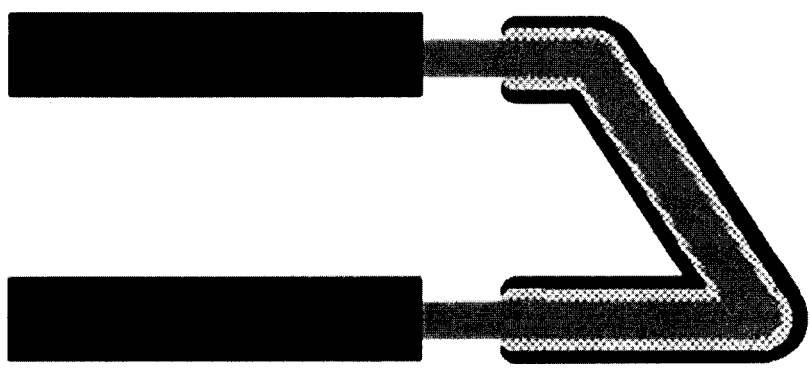
Figure 6C:
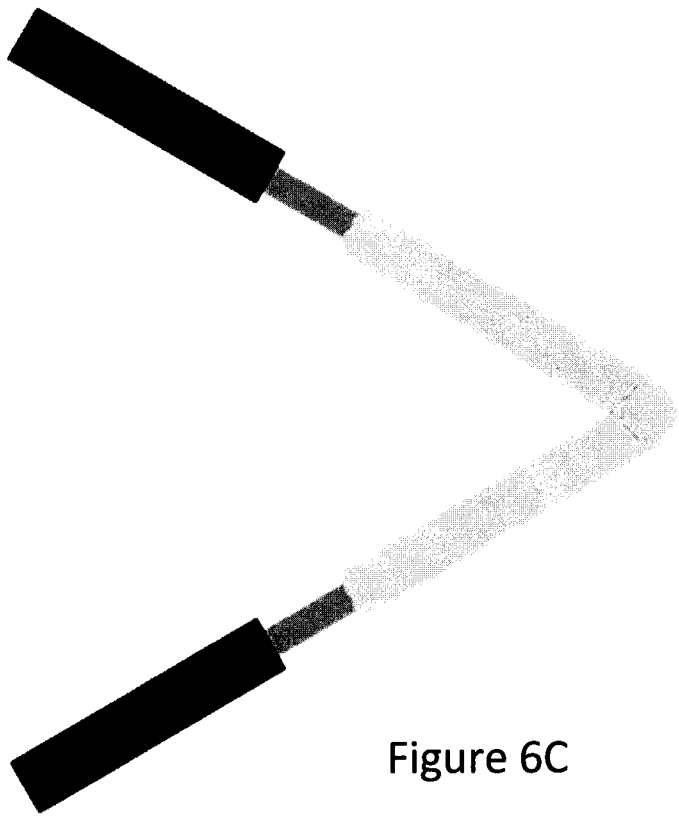
Figure 6D:
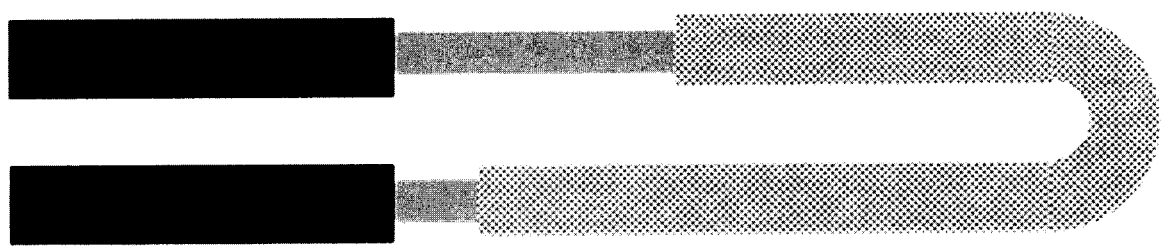

FIGS. 6A and 6B show double-bend configurations, which is covered by a glass layer in FIG. 6B. FIGS. 6C and 6D show single-bend configurations of different angles.

Compared to FIG. 5, the examples of FIG. 6 do not require polishing (e.g., end polished or side polished). In the examples of FIG. 6, the plasmonic optical fiber 1600 is bent and coated with a gold layer (e.g., can vary from 20 to 50 nm with 40 nm giving expected sensitivity and mechanical strength).

One or several bent area and angles may be provided on a single fiber in order to excite surface plasmon in a sensing area. With the configurations of FIG. 6, it is also easier to predictably determine the angle at which the optical signal conveyed on the fiber hits the gold layer in order to excite surface plasmon waves on top of gold layer (e.g., for humidity and gas sensing). When polishing is used, the tip of the fiber is expected to be polished at a specific angle around 45 degree.

In the configurations of FIG. 6, by varying the angle of the one or more bent in the fiber from 180 to 0, the sensitivity of fiber may be predictably determined. It has been shown that angles between 90 and 30 degrees provide better results, with a peak sensitivity around in 60 degrees. An optimum bending angle may be set from careful consideration of different parameters. For instance, the optimum angle depends on the refractive index of the environment adjacent to gold layer. The refractive index of air and humidity or gases is around 1 and the angle therefore needs to be tighter to excite surface plasmon. When sensing inside water with refractive index of 1.33, the bend angle can be looser (up to around 180 degrees).

The optimum angle also depends of operation spectrum or wavelength. For instance, a white source (visible range 500-900 nm) may be used to excite surface plasmon in air, because it is easier to excite surface Plasmon in lower wavelength. In order to excite surface plasmon in higher wavelength (IR, telecom range 1330 to 1600 nm) range, a sharper light incident to gold layer is required and the fiber therefore needs to be bend in a sharper angle (e.g., less than 60 degree). The optimum angle also depends on the type of optical fiber. Typically, the larger the core of optical fiber, the more optical modes can be guided therein. Each mode has its unique angle of incident and surface plasmon can therefore be excited with a specific mode having specific angle of incident for a specific bend area. Four (4) types of multi-mode fiber have been testes with core diameters of 200, 400, 600, 1000 micron. The maximum sensitivity has been observed in 600-micron fiber that happened at the angle of 60 degree (e.g., FIG. 6C). Using a 600-micron fiber with two bends of 60 and 120 degree as depicted in FIGS. 6A and 6B allow for more versatile sensing. While more than two bends may be made in the fiber, more optical loss are caused and it may only be suitable for high power sources.

The sensing area 1610 may be covered with one or several layers of coating. In some embodiments, all coatings are done with the standard coating equipment compatible with the semiconductor industry and generally available in microfabrication labs. Different types of optical fibers may be used, whether they are made of glass or polymer. Cladding over the fiber core may or may not be removed. Different fiber core diameters may also be used such as 200, 400, 600, and 1000 microns. Different light sources may be selected (e.g., visible, IR or others area of light spectrum) depending on the bent and coating area. Visible & IR spectrum in range 450 nm to 900 nm have been tested and 500 to 900 nm sensors could operate while losing limited sensitivity and accuracy. Very low cost LED light source may therefore effectively be used leading to low cost for sensor to operate a wavelength of choice. Because embodiments of the present invention are based on optical transmission loss, it is possible to develop a processing module (e.g., an interrogator box that converts optics to electronics) at low cost as well. The fiber bending process is also easily repeatable and does not involve a costly polishing process. It is possible to automate the fiber bending process for mass production.

When the target molecule is a gas (i.e., for gas sensing), the principle and bending process remain the same and additional coating are typically added on top of the gold layer. For example, for hydrogen sensing, a palladium and silver or tantalum coating is added on the bent fiber.

The embodiments of the present invention also support "Drift free Sensors" since the sensitivity of surface plasmon is not affected by time duration and a probe is made of gold and glass is able to sustain harsh and normal environment.

It is possible to develop fast response sensors in accordance with some embodiments of the present invention. The response time depends on the response time of the light and surface plasmon waves, which are very fast.

Figure 2:
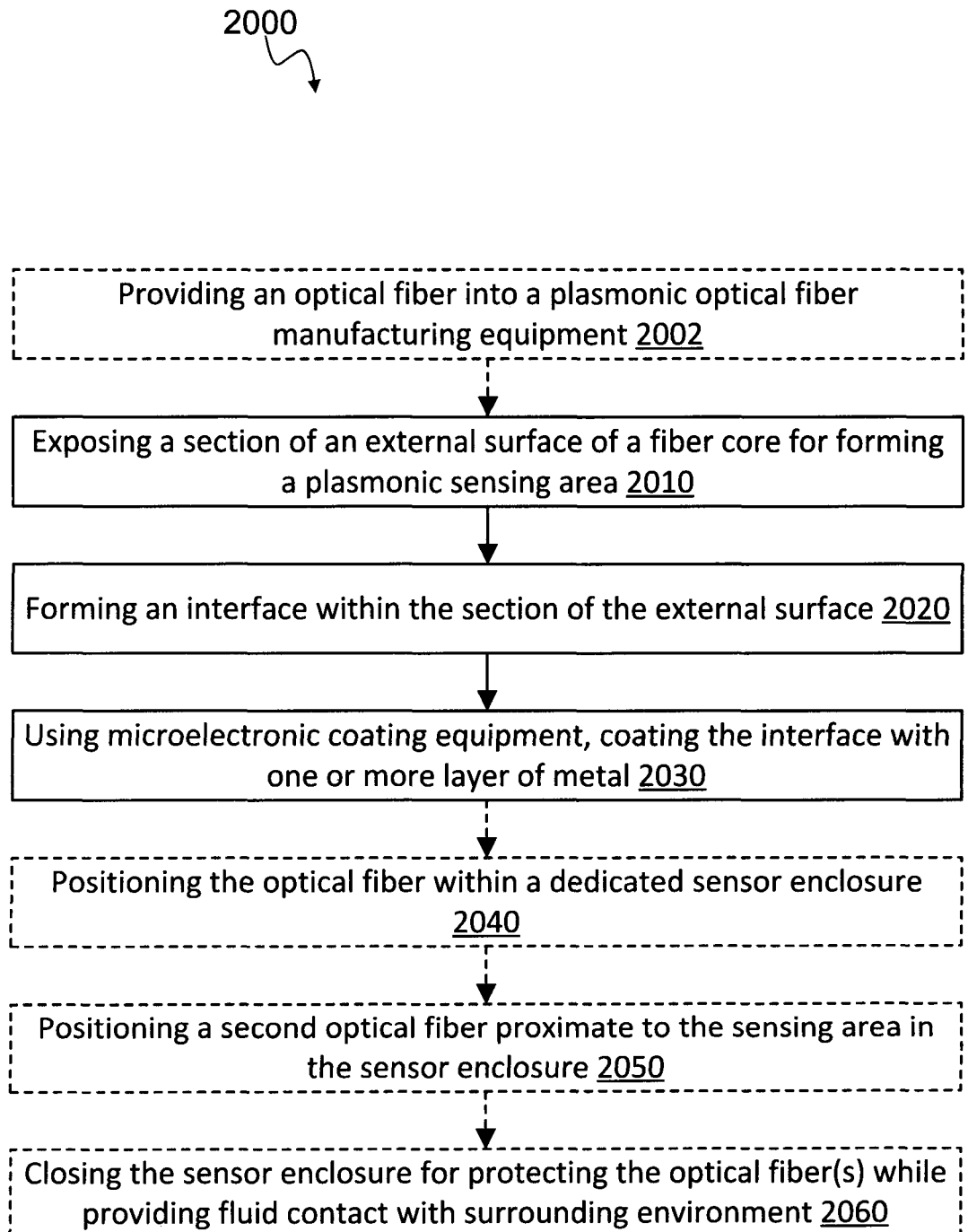
FIG. 2 is a flow chart of an exemplary manufacturing method in accordance with the teachings of the present invention.

FIG. 2 shows a flow chart of an exemplary method 2000 for manufacturing a plasmonic optical fiber and, optionally, a plasmonic optical sensor. The method 2000 main first start with providing 2002 an optical fiber to a manufacturing equipment. The method 2000 comprises exposing 2010 a section of an external surface of a fiber core from the optical fiber for forming a plasmonic sensing area, forming 2020 an interface within the section of the external surface such that a signal conveyed in the fiber core at least partially exits the fiber core and, using microelectronic coating equipment, coating 2030 the interface with one or more layer of metal.

Forming 2020 the interface may optionally further comprise bending the exposed section of the external surface in excess of a critical angle that ensures total internal reflection of the conveyed signal therewithin. Forming 2020 the interface may alternatively further comprise cutting the fiber core for forming the interface at an open thereof.

Coating 2030 the interface with one or more layer of metal may further comprise applying a gold layer before one or more additional layer.

The method 2000 may also comprise providing a fluid-permeable enclosure, positioning 2040 the plasmonic optical fiber in the enclosure for the sensing area to be in contact with the fluid and closing the enclosure for protecting the plasmonic optical fiber housed therein. The method 2000 may further comprise positioning 2050 a second optical fiber proximate to the sensing area in the enclosure before closing 2060 the enclosure for protecting the plasmonic optical fiber and the second optical fiber housed therein.

The description of the present invention has been presented for purposes of illustration but is not intended to be exhaustive or limited to the disclosed embodiments. Many modifications and variations will be apparent to those of ordinary skill in the art. The embodiments were chosen to explain the principles of the invention and its practical applications and to enable others of ordinary skill in the art to understand the invention in order to implement various embodiments with various modifications as might be suited to other contemplated uses.

What is claimed is:

1. A plasmonic optical sensor comprising:
   a plasmonic optical fiber comprising a fiber core for conveying an optical signal therewithin, the fiber core having a terminal end providing a plasmonic sensing area at the terminal end and configured to be exposed to a fluid, the plasmonic sensing area being formed only on a section of an external surface of the fiber core; and wherein the plasmonic sensing area provides an interface within the section of the external surface for the conveyed signal to at least partially exit the fiber core;
   an optical signal generator for providing the optical signal to the plasmonic optical fiber;
   a non-plasmonic optical fiber a spaced distance from and proximate to the plasmonic sensing area at the terminal end of the plasmonic optical fiber, wherein the non-plasmonic optical fiber conveys a modified optical signal from the conveyed signal at least partially exiting the fiber core;
   an optical signal receiver that receives the modified optical signal from the non-plasmonic optical fiber; and
   a processor module that analyzes the modified optical signal and identifies one or more physical characteristics of the fluid present at the sensing area.

2. The plasmonic optical sensor of claim 1, further comprising a fluid-permeable enclosure for housing the plasmonic optical fiber while the sensing area is in contact with the fluid.

3. A method of manufacturing a plasmonic optical sensor apparatus comprising:
   providing a fluid-permeable enclosure;
   positioning the plasmonic optical sensor in accordance with claim 1 in the enclosure for the sensing area to be in contact with the fluid;
   closing the enclosure for protecting the plasmonic optical sensor housed therein.

4. The plasmonic optical sensor of claim 1, wherein the plasmonic optical fiber further comprises a fiber cladding for preventing the conveyed optical signal in the fiber core from exiting therefrom outside of the section of the external surface of the fiber core.

5. The plasmonic optical sensor of claim 1, wherein the interface of the plasmonic sensing area is formed by one or more layers of material formed thereon.

6. The plasmonic optical fiber of claim 5, wherein the one or more layers comprises a deposited gold layer for sensing presence of specific molecules in the fluid.

7. The plasmonic optical fiber of claim 6, wherein the gold layer is between 20 nm and 50 nm thick for sensing presence of water molecules in the fluid.

8. The plasmonic optical fiber of claim 6, wherein the one or more layer further comprises a deposited palladium layer for sensing presence of hydrogen in the fluid.

9. The plasmonic optical fiber of claim 8, wherein the one or more layer further comprises a deposited silver layer or tantalum layer over the gold layer for sensing presence of hydrogen in the fluid.

10. The plasmonic optical fiber of claim 9, wherein the silver layer or tantalum layer is 10 to 30 nm thick.

11. The plasmonic optical fiber of claim 8, wherein the palladium layer is 150 to 350 nm thick.

* * * * *